United States Patent
Fujihira et al.

(10) Patent No.: US 10,506,759 B2
(45) Date of Patent: Dec. 17, 2019

(54) RICE SEED TREATMENT AGENT

(71) Applicant: KUMIAI CHEMICAL INDUSTRY CO., LTD., Tokyo (JP)

(72) Inventors: Yoshitaka Fujihira, Tokyo (JP); Satoshi Watanabe, Tokyo (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 14 days.

(21) Appl. No.: 15/771,508

(22) PCT Filed: Oct. 20, 2016

(86) PCT No.: PCT/JP2016/081116
§ 371 (c)(1),
(2) Date: Apr. 27, 2018

(87) PCT Pub. No.: WO2017/073452
PCT Pub. Date: May 4, 2017

(65) Prior Publication Data
US 2018/0343787 A1    Dec. 6, 2018

(30) Foreign Application Priority Data
Oct. 30, 2015  (JP) ................................ 2015-215259

(51) Int. Cl.
| A01C 1/06 | (2006.01) |
| A01C 1/08 | (2006.01) |
| A01N 43/54 | (2006.01) |
| A01N 43/60 | (2006.01) |
| A01N 47/36 | (2006.01) |
| A01N 25/04 | (2006.01) |

(52) U.S. Cl.
CPC ................ *A01C 1/06* (2013.01); *A01C 1/08* (2013.01); *A01N 43/54* (2013.01); *A01N 43/60* (2013.01); *A01N 47/36* (2013.01); *A01N 25/04* (2013.01)

(58) Field of Classification Search
CPC .......... A01N 43/40; A01N 25/00; A01C 1/06; A01C 1/08
See application file for complete search history.

(56) References Cited

U.S. PATENT DOCUMENTS

| 4,808,430 A * | 2/1989 | Kouno ..................... A01C 1/06 427/350 |
| 2010/0323886 A1 | 12/2010 | Voeste et al. |
| 2016/0120182 A1 | 5/2016 | Tamaru et al. |

FOREIGN PATENT DOCUMENTS

| JP | 2009-249358 | 10/2009 |
| JP | 2011-510957 | 4/2011 |
| WO | 01/13722 | 3/2001 |
| WO | 2009/124708 | 10/2009 |
| WO | WO-2013176282 A1 * | 11/2013 ............. A01N 47/36 |
| WO | 2014/189126 | 11/2014 |
| WO | 2017/065014 | 4/2017 |

OTHER PUBLICATIONS

International Search Report dated Nov. 15, 2016 in International Application No. PCT/JP2016/081116.
Yuta Amano et al., Proceedings, the 40th Annual Meeting of the Pesticide Science Society of Japan, Mar. 18, 2015, vol. 40, p. 84, with partial English translation.
Extended European Search Report dated May 24, 2019 in corresponding European Patent Application No. 16859682.3.

* cited by examiner

*Primary Examiner* — Johann R Richter
*Assistant Examiner* — Danielle Sullivan
(74) *Attorney, Agent, or Firm* — Wenderoth, Lind & Ponack, L.L.P.

(57) ABSTRACT

A paddy seed treatment agent containing a herbicidal active component and having a sufficient herbicidal effect, while having a reduced risk of herbicide injury to paddy rice, a method for treating paddy seeds using the paddy seed treatment agent, paddy seeds, and a method for controlling paddy field weeds by sowing and cultivating the paddy seeds, are provided. The paddy seed treatment agent contains fenquinotrione or a salt thereof as a herbicidal active component. The method for controlling paddy field weeds includes sowing and cultivating paddy seeds treated with this paddy seed treatment agent, and the like.

11 Claims, No Drawings

US 10,506,759 B2

RICE SEED TREATMENT AGENT

TECHNICAL FIELD

The present invention relates to a paddy seed treatment agent, a method for treating paddy seeds using the same, paddy seeds, and a method for controlling paddy field weeds; more specifically, relates to a paddy seed treatment agent containing a herbicidal active component and having a sufficient herbicidal effect, while having a reduced risk of herbicide injury to paddy rice, a method for treating paddy seeds using the paddy seed treatment agent, paddy seeds, and a method for controlling paddy field weeds by sowing and cultivating the paddy seeds.

BACKGROUND ART

One major problem in paddy cultivation is control of weeds growing in paddy fields. From ancient times, people spent a lot of time and labor for control of paddy field weeds. However, excellent herbicides have been practically used in recent years, and are largely contributing to labor saving and increased production in paddy cultivation.

At present, in herbicides used for controlling paddy field weeds, various compounds such as bleaching herbicidal active compounds, acetolactate synthase-inhibiting herbicidal active compounds, protoporphyrinogen oxidase-inhibiting herbicidal active compounds, and very-long-chain fatty acid elongase-inhibiting herbicidal active compounds are used as effective components, and there are a number of products. These are usually used by spraying on paddy fields at the same time as transplantation of paddy seedlings, or in the initial phase of the growth of weeds. However, treatment of entire large areas of paddy fields using these herbicides is never easy, and the treatment period overlaps with the busy period of paddy field work. Thus, further labor saving has been demanded.

As a cultivation method for paddy rice other than transplantation cultivation, direct sowing cultivation, in which paddy seeds are directly sown on a paddy field, is carried out. In direct sowing cultivation, the cultivation period in paddy fields is longer than that in transplantation cultivation. Therefore, weeds need to be controlled for a longer period, and there is a problem that spraying of herbicides needs to be carried out a larger number of times.

As methods for saving the labor of control using a pesticide, methods in which seeds before sowing are treated with a pesticide is known. In cases of some microbicides, insecticides, and plant growth regulators, seed treatment agents containing them are now being practically used (Patent Documents 1 to 3)

RELATED ART DOCUMENTS

Patent Documents

[Patent Document 1] Japanese Unexamined Patent Application Publication No. 2009-249358
[Patent Document 2] WO 01/13722
[Patent Document 3] Japanese Unexamined Patent Application Publication (Translation of PCT Application) No. 2011-510957

SUMMARY OF THE INVENTION

Problems to be Solved by the Invention

However, paddy seed treatment agents containing a herbicide have not been practically used. This is because microbicides, insecticides, and plant growth regulators exert their effects by absorption of their effective component compounds into crop seeds, while herbicides exert their effects by absorption into weeds, so that, due to the presence of the herbicide used for the treatment of seeds in the vicinity of the seeds at a high concentration, herbicide injury to the paddy rice itself may occur, and a sufficient herbicidal effect can be hardly obtained in areas distant from the seeds.

In view of this, the present invention was made for the purpose of providing a paddy seed treatment agent containing a herbicidal active component and having a sufficient herbicidal effect, while having a reduced risk of herbicide injury to paddy rice, a method for treating paddy seeds using the same, paddy seeds, and a method for controlling paddy field weeds.

Means for Solving the Problems

In order to solve the above problem, the present inventors intensively studied to discover surprisingly that, in cases where fenquinotrione or a salt thereof is used as a herbicidal active component in a seed treatment agent, fenquinotrione is dispersed in a paddy field through flood water, and a sufficient herbicidal effect can be obtained throughout the paddy field, while the risk of herbicide injury to paddy rice can be reduced, thereby completing the present invention.

That is, the present invention is as follows.
(1) A paddy seed treatment agent comprising fenquinotrione or a salt thereof as a herbicidal active component.
(2) The paddy seed treatment agent according to (1), further comprising an acetolactate synthase-inhibiting herbicidal active compound or a salt thereof as a herbicidal active component.
(3) The paddy seed treatment agent according to (2), wherein the acetolactate synthase-inhibiting herbicidal active compound is one or more compounds selected from the group consisting of sulfonyl urea compounds, imidazolinone compounds, triazolopyrimidine compounds, pyrimidinyl carboxy compounds, and sulfonylaminocarbonyltriazolinone compounds.
(4) The paddy seed treatment agent according to (3), wherein the pyrimidinyl carboxy compound is pyrimisulfan.
(5) The paddy seed treatment agent according to any one of (1) to (4), further comprising one or more coating agents selected from the group consisting of iron powders, calcium peroxide, and molybdenum compounds.
(6) A method for treating a paddy seed(s), the method comprising treating a paddy seed(s) using the paddy seed treatment agent according to any one of (1) to (5).
(7) The method for treating a paddy seed(s) according to (6), wherein the paddy seed treatment agent further comprises an acetolactate synthase-inhibiting herbicidal active compound or a salt thereof as a herbicidal active component.
(8) The method for treating a paddy seed(s) according to (6) or (7), wherein the paddy seed(s) is/are treated with the paddy seed treatment agent in an amount in which the amount of the fenquinotrione or a salt thereof is within the range of 0.01 g to 3000 g per 1 kg of the paddy seed(s).
(9) The method for treating a paddy seed(s) according to (7) or (8), wherein the paddy seed(s) is/are treated with the paddy seed treatment agent in an amount in which the amount of the acetolactate synthase-inhibiting herbicidal active compound or a salt thereof is within the range of 0.01 g to 3000 g per 1 kg of the paddy seed(s).
(10) The method for treating a paddy seed(s) according to any one of (6) to (9), wherein, after the treatment of the paddy seed(s) with the paddy seed treatment agent, coating treatment with one or more coating agents selected from the group consisting of iron powders, calcium peroxide, and molybdenum compounds is carried out.

(11) The method for treating a paddy seed(s) according to any one of (6) to (9), wherein, before the treatment of the paddy seed(s) with the paddy seed treatment agent, coating treatment with one or more coating agents selected from the group consisting of iron powders, calcium peroxide, and molybdenum compounds is carried out.

(12) The method for treating a paddy seed(s) according to any one of (6) to (9), wherein the paddy seed treatment agent is mixed with one or more coating agents selected from the group consisting of iron powders, calcium peroxide, and molybdenum compounds, and the paddy seed(s) is/are subjected to coating treatment with the resulting mixture.

(13) A paddy seed(s) treated with the paddy seed treatment agent according to any one of (1) to (5).

(14) A method for controlling paddy field weeds, the method comprising sowing and cultivating the paddy seed(s) according to (13).

Effect of the Invention

According to the present invention, a paddy seed treatment agent containing a herbicidal active component and having a sufficient herbicidal effect, while having a reduced risk of herbicide injury to paddy rice, can be realized.

MODE FOR CARRYING OUT THE INVENTION

The paddy seed treatment agent, the method for treating paddy seeds, the paddy seeds, and the method for controlling paddy field weeds, of the present invention are described below in detail.

The paddy seed treatment agent of the present invention comprises fenquinotrione or a salt thereof as a herbicidal active component.

The fenquinotrione used in the present invention is a known substance described in WO 2009/016841 having the structure represented by the following formula, and can be produced by a method described in WO 2009/016841.

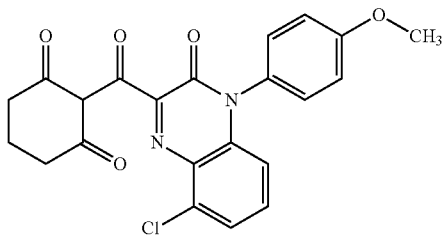 [SMILES: COc1ccc(-n2c(=O)c(C(=O)C3C(=O)CCCC3=O)nc3c(Cl)cccc32)cc1]

The content (total content, in cases where two or more types are contained) of the fenquinotrione or a salt thereof contained in the paddy seed treatment agent of the present invention may be selected as appropriate depending on an arbitrary component(s) contained in the paddy seed treatment agent and the formulation used, and is usually within the range of 0.01 to 99% by mass, preferably 0.1 to 95% by mass in the paddy seed treatment agent.

The paddy seed treatment agent of the present invention may further contain an acetolactate synthase-inhibiting herbicidal active compound or a salt thereof as a herbicidal active component. The acetolactate synthase-inhibiting herbicidal active compound or a salt thereof used in the present invention belongs to a group of compounds well known to those skilled in the art which inhibit plant acetolactate synthase to inhibit synthesis of essential amino acids valine, leucine, and isoleucine, thereby killing weeds. As acetolactate synthase-inhibiting herbicidal active compounds, sulfonyl urea compounds, imidazolinone compounds, triazolopyrimidine compounds, pyrimidinyl carboxy compounds, and sulfonylaminocarbonyltriazolinone compounds are widely known. In the present invention, one or more acetolactate synthase-inhibiting herbicidal active compounds selected from these compounds may be used.

Examples of the sulfonyl urea compound include amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfuron, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl and tritosulfuron.

Examples of the imidazolinone compound include imazapic (including its salts with amines, e.g.), imazamethabenz-methyl, imazamox (including its salts with amines, e.g.), imazapyr (including its isopropylamine salt, e.g.) and imazaquin, imazethapyr (including its salts with amines, e.g.).

Examples of the triazolopyrimidine compound include cloransulam-methyl, diclosulam, florasulam, flumetsulam, metosulam, penoxsulam and pyroxsulam.

Examples of the pyrimidinyl carboxy compound include bispyribac-sodium, pyribenzoxim, pyrithiobac-sodium, pyriftalid, pyriminobac-methyl and pyrimisulfan.

Examples of the sulfonylaminocarbonyltriazolinone compound include flucarbazone-sodium, propoxycarbazone-sodium and thiencarbazone (including its sodium salt or methyl ester, e.g.).

All of the above-described acetolactate synthase-inhibiting herbicidal active compounds are known from, for example, The Pesticide Manual 16th Edition, published by British Crop Production Council; and World of Herbicides Map (http://www.hracglobal.com/pages/world%20of%20herbicides%20map.aspx), published by Herbicide Resistance Action Committee.

Among the acetolactate synthase-inhibiting herbicidal active compounds, sulfonyl urea compounds and pyrimidinyl carboxy compounds are preferred. Bensulfuron-methyl, pyrimisulfan, and pyriminobac-methyl are more preferred. Pyrimisulfan is especially preferred.

The content (total content, in cases where two or more types are contained) of the acetolactate synthase-inhibiting herbicidal active compound contained in the paddy seed treatment agent of the present invention may be selected as appropriate depending on an arbitrary component(s) contained in the paddy seed treatment agent and the formulation used, and is usually within the range of 0.01 to 99% by mass, preferably 0.1 to 95% by mass in the paddy seed treatment agent. In cases where pyrimisulfan is used as the acetolactate synthase-inhibiting herbicidal active compound, the content of the pyrimisulfan in the paddy seed treatment agent of the present invention may be selected such that its ratio is 0.01 to 10, more preferably 0.01 to 1 with respect to the content (total content, in cases where two or more types are contained) of the fenquinotrione or a salt thereof, which is taken as 1.

The paddy seed treatment agent of the present invention may contain a coating agent which is a material conventionally used for direct sowing cultivation and the like. Examples of the coating agent include iron powders, calcium peroxide, and molybdenum compounds. For the paddy seed treatment agent of the present invention, one or more coating agents selected from these may be used. An iron powder is preferably used.

The paddy seed treatment agent of the present invention may further contain, as another pesticidal active component, a microbicide, insecticide, acaricide, nematicide, or plant growth regulator. Examples of such a microbicide include, but are not limited to, strobilurin compounds, anilinopyrimidine compounds, azole compounds, dithiocarbamate compounds, phenylcarbamate compounds, organochlorine compounds, benzimidazole compounds, phenylamide compounds, sulfenic acid compounds, copper compounds, isoxazole compounds, organophosphorus compounds, N-halogenothioalkyl compounds, carboxyanilide compounds, morpholine compounds, organotin compounds, and/or cyanopyrrole compounds. Examples of the insecticide, acaricide, and nematicide include, but are not limited to, pyrethroid compounds, organophosphorus compounds, oxime carbamate compounds, carbamate compounds, neonicotinoid compounds, diacylhydrazine compounds, benzoylurea compounds, juvenile hormone compounds, cyclodiene organochlorine compounds, 2-dimethylaminopropane-1,3-dithiol compounds, amidine compounds, phenylpyrazole compounds, organotin compounds, METI compounds, benzylate compounds, allylpyrrole compounds, dinitrophenol compounds, anthranilic diamide compounds, oxadiazine compounds, semicarbazone compounds, tetronic acid compounds, carbamoyl triazole compounds, and tetrazine compounds.

More specific examples of the compounds include the following.

Examples of the microbicide include azaconazole, acibenzolar-S-methyl, azoxystrobin, anilazine, amisulbrom, ametoctradin, aldimorph, isotianil, isopyrazam, isofetamid, isoprothiolane, ipconazole, iprodione, iprovalicarb, iprobenfos, imazalil, iminoctadine-tris-albesilate, iminoctadine-triacetate, imibenconazole, edifenphos, etaconazole, ethaboxam, ethirimol, ethoxyquin, etridiazole, enestroburin, enoxastrobin, epoxiconazole, organic oils, oxadixyl, oxazinylazole, oxathiapiprolin, oxycarboxin, oxine-copper, oxytetracycline, oxpoconazole-fumarate, oxolinic acid, copper dioctanoate, octhilinone, ofurace, orysastrobin, o-phenylphenol, kasugamycin, captafol, carpropamid, carbendazim, carboxin, carvone, quinoxyfen, chinomethionat, captan, quinconazole, quintozene, guazatine, cufraneb, coumoxystrobin, kresoxim-methyl, clozylacon, chlozolinate, chlorothalonil, chloroneb, cyazofamid, diethofencarb, diclocymet, dichlofluanid, diclomezine, dicloran, dichlorophen, dithianon, diniconazole, diniconazole-M, zineb, dinocap, dipymetitrone, diphenylamine, difenoconazole, cyflufenamid, diflumetorim, cyproconazole, cyprodinil, simeconazole, dimethirimol, dimethyl disulfide, dimethomorph, cymoxanil, dimoxystrobin, ziram, silthiofam, streptomycin, spiroxamine, sedaxane, zoxamide, dazomet, tiadinil, thiabendazole, thiram, thiophanate, thiophanate-methyl, thifluzamide, tecnazene, tecloftalam, tetraconazole, debacarb, tebuconazole, tebufloquin, terbinafine, dodine, dodemorph, triadimenol, triadimefon, triazoxide, trichlamide, triclopyricarb, tricyclazole, triticonazole, tridemorph, triflumizole, trifloxystrobin, triforine, tolylfluanid, tolclofos-methyl, tolnifanide, tolprocarb, nabam, natamycin, naftifine, nitrapyrin, nitrothal-isopropyl, nuarimol, copper nonyl phenol sulphonate, *Bacillus subtilis* (strain: QST 713), validamycin, valifenalate, picarbutrazox, bixafen, picoxystrobin, pydiflumetofen, bitertanol, binapacryl, biphenyl, piperalin, hymexazol, pyraoxystrobin, pyraclostrobin, pyraziflumid, pyrazophos, pyrametostrobin, pyriofenone, pyrisoxazole, pyrifenox, pyributicarb, pyribencarb, pyrimethanil, pyroquilon, vinclozolin, ferbam, famoxadone, phenazine oxide, fenamidone, fenaminstrobin, fenarimol, fenoxanil, ferimzone, fenpiclonil, fenpyrazamine, fenbuconazole, fenfuram, fenpropidin, fenpropimorph, fenhexamid, folpet, phthalide, bupirimate, fuberidazole, blasticidin-S, furametpyr, furalaxyl, furancarboxylic acid, fluazinam, fluindapyr, fluoxastrobin, fluopicolide, fluopyram, fluoroimide, fluxapyroxad, fluquinconazole, furconazole, furconazole-cis, fludioxonil, flusilazole, flusulfamide, flutianil, flutolanil, flutriafol, flufenoxystrobin, flumetover, flumorph, proquinazid, prochloraz, procymidone, prothiocarb, prothioconazole, bronopol, propamocarb-hydrochloride, propiconazole, propineb, probenazole, bromuconazole, flometoquin, hexaconazole, benalaxyl, benalaxyl-M, benodanil, benomyl, pefurazoate, penconazole, pencycuron, benzovindiflupyr, benthiazole, benthiavalicarb-isopropyl, penthiopyrad, penflufen, boscalid, fosetyl (alminium, calcium, sodium), polyoxin, polycarbamate, Bordeaux mixture, mancozeb, mandipropamid, mandestrobin, maneb, myclobutanil, mineral oils, mildiomycin, methasulfocarb, metam, metalaxyl, metalaxyl-M, metiram, metconazole, metominostrobin, metrafenone, mepanipyrim, meptyldinocap, mepronil, iodocarb, laminarin, phosphorous acid and salts, copper oxychloride, silver, cuprous oxide, copper hydroxide, potassium bicarbonate, sodium bicarbonate, sulfur, oxyquinoline sulfate, copper sulfate, (3,4-dichloroisothiazole-5-yl) methyl-4-(tert-butyl)benzoate (IUPAC Name, CAS No. 1231214-23-5), 3-((3,4-dichloroisothiazole-5-yl)methoxy)benzo[d] isothiazole-1,1-dioxide (IUPAC Name, CAS No. 957144-77-3), BAF-045 (Code No.), BAG-010 (Code No.), UK-2A (Code No.), DBEDC (dodecylbenzenesulphonic acid bisethylenediamine copper [II] salt), MIF-1002 (Code No.), TPTA (fentin-acetate), TPTC (triphenyltin chloride), TPTH (fentin hydroxide), nonpathogenic *Envinia carotovora*, and the like.

Examples of the insecticide, acaricide, and nematicide include acrinathrin, azadirachtin, azamethiphos, azinphosethyl, azinphos-methyl, acequinocyl, acetamiprid, acetoprole, acephate, azocyclotin, abamectin, afidopyropen, afoxolaner, amidoflumet, amitraz, alanycarb, aldicarb, aldoxycarb, allethrin (including its d-cis-trans body and d-trans body), isazophos, isamidofos, isocarbophos, isoxathion, isofenphos-methyl, isoprocarb, ivermectin, imicyafos, imidacloprid, imiprothrin, indoxacarb, esfenvalerate, ethiofencarb, ethion, ethiprole, ethylene dibromide, etoxazole, etofenprox, ethoprophos, etrimfos, emamectin benzoate, endosulfan, empenthrin, oxamyl, oxydemeton-methyl, oxydeprofos, omethoate, cadusafos, kappa-tefluthrin, kappa-bifenthrin, karanjin, cartap, carbaryl, carbosulfan, carbofuran, gamma-BHC, xylylcarb, quinalphos, kinoprene, chinomethionat, coumaphos, cryolite, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, chloroprallethrin, cyanophos, diafenthiuron, diamidafos, cyantraniliprole, dienochlor, cyenopyrafen, dioxabenzofos, diofenolan, cyclaniliprole, dicrotophos, dichlofenthi on, cycloprothrin, dichlorvos, 1,3-dichloropropene, dichloromezoti az, dicofol, dicyclanil, disulfoton, dinotefuran, dinobuton, cyhalodiamide, cyhalothrin (including its gamma-body and lambda-body), cyphenothrin (including its (1R)-trans-body), cyfluthrin (including its beta-body), diflubenzuron, cyflumetofen, diflovidazin, cyhexatin, cypermethrin (including its alpha-body, beta-body, theta-body, and zeta-body), dimethylvinphos, dimefluthrin, dimethoate, silafluofen, cyromazine, spinetoram, spinosad, spirodiclofen, spirotetramat, spiromesifen, sulcofuron-sodium, sulfluramid, sulfoxaflor, sulfotep, diazinon, thiacloprid, thiamethoxam, tioxazafen, thiodicarb, thiocyclam, thiosultap, thionazin, thiofanox, thiometon, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, triflumezopyrim, trimethacarb, tolfenpyrad, naled, nitenpyram, novaluron, noviflumuron, *Verticillium lecanii*, hydroprene, Pasteuriapenetrans, vamidothion, parathion, parathion-methyl, halfenprox, halofenozide, bioallethrin, bioallethrin S-cyclopentenyl, bioresmethrin, bistrifluron, hydramethylnon, bifenazate, bifenthrin, pyflubumide, piperonyl butoxide, pymetrozine, pyraclofos, pyrafluprole, pyridaphenthion, pyridaben, pyridalyl, pyrifluquinazon, pyriprole, pyriproxyfen, pirimicarb, pyrimidifen, pyriminostrobin, pirimiphos-methyl, pyrethrine, famphur, fipronil, fenazaquin, fenamiphos, fenitrothion, fenoxycarb, fenothiocarb, phenothrin (including its (1R)-trans-body), fenobucarb, fenthion, phenthoate, fenvalerate, fenpyroximate, fenbutatin oxide, fenpropathrin, fonofos, sulfuryl fluoride, butocarboxim, butoxycarboxim, buprofezin, furathiocarb, prallethrin, fluacrypyrim, fluazaindolizine, fluazuron, fluensulfone, sodium fluoroacetate, fluxametamide, flucycloxuron, flucythrinate, flusulfamide, fluvalinate (including its tau-body), flupyradifurone, flupyrazofos, flufiprole, flufenerim, flufenoxystrobin, flufenoxuron, fluhexafon, flubendiamide, flumethrin, fluralaner, prothiofos, protrifenbute, flonicamid, propaphos, propargite, profenofos, broflanilide, profluthrin, propetamphos, propoxur, flometoquin, bromopropylate, hexythiazox, hexaflumuron, *Paecilomyces tenuipes*, *Paecilomyces fumosoroceus*, heptafluthrin, heptenophos, permethrin, benclothiaz, bensultap, benzoximate, bendiocarb, benfuracarb, *Beauveria tenella*, *Beauveria bassiana*, *Beauveria brongniartii*, phoxim, phosalone, fosthiazate, fosthietan, phosphamidon, phosmet, polynactins, formetanate, phorate, malathion, milbemectin, mecarbam, mesulfenfos, methoprene, methomyl, metaflumizone, methamidophos, metham, methiocarb, methidathion, methyl isothiocyanate, methyl bromide, methoxychlor, methoxyfenozide, methothrin, metofluthrin, epsilon-metofluthrin, methoprene, metolcarb, mevinphos, meperfluthrin, Monacrosporium phymatophagum, monocrotophos, momfluorothrin, epsilon-momfluorothrin, litlure-A, litlure-B, aluminium phosphide, zinc phosphide, phosphine, lufenuron, rescalure, resmethrin, lepimectin, rotenone, fenbutatin oxide, calcium cyanide, nicotinesulfate, (Z)-11-tetradecenyl acetate, (Z)-11-hexadecenal, (Z)-11-hexadecenyl acetate, (Z)-9,12-tetradecadienyl acetate, (Z)-9-tetradecen-1-ol, (Z,E)-9,11-tetradecadienyl acetate, (Z,E)-9,12-tetradecadienyl acetate, *Bacillus popilliae, Bacillus subtillis, Bacillus sphaericus, Bacillus thuringiensis* subsp. *Aizawai, Bacillus thuringiensis* subsp. *Israelensis, Bacillus thuringiensis* subsp. *Kurstaki, Bacillus thuringiensis* subsp. *Tenebrionis*, Bt proteins (Cry1Ab, Cry1Ac, Cry1Fa, Cry2Ab, mCry3A, Cry3Ab, Cry3Bb, Cry34/35Ab1), CL900167 (Code No.), DCIP (bis-(2-chloro-1-methylethyl)ether), DDT (1,1,1-trichloro-2,2-bis (4-chlorophenyl) ethane), DEP (dimethyl-2,2,2-trichloro-1-hydroxyethylphosphonate), DNOC (4,6-dinitro-o-cresol), DSP (O,O-diethyl-O-[4-dimethylsulfamoyl]phenyl) phosphorothioate), EPN (O-ethyl O-(4-nitrophenyl) phenylphosphonothioate), nuclear polyhedrosis virus occlusion body, NA-85 (Code No.), NA-89 (Code No.), NC-515 (Code No.), RU15525 (Code No.), ZDI-2501 (Code No.), XMC, Z-13-eicosene-10-one, ZXI8901 (Code No.), and ME5382 (Code No.).

Examples of the plant growth regulator include 1-naphthylacetamide, 1-methylcyclopropene, 2,6-diisopropylnaphthalene, 4-CPA (4-chlorophenoxy) acetic acid), 4-oxo-4-(2-phenylethyl) aminobutyric acid (IUPAC Name, CAS No. 1083-55-2), n-decanol, aviglycine, ancymidol, inabenfide, indole acetic acid, indole butyric acid, uniconazole, uniconazole-P, ethychlozate, ethephon, epocholeone, carvone, cloxyfonac, cloxyfonac-potassium, cloprop, chlormequat, cytokinins, cyclanilide, dikegulac, gibberellins, dimethipin, sintofen, daminozide, thidiazuron, triacontanol, trinexapac-ethyl, paclobutrazol, flumetralin, flurprimidol, flurenol, prohydrojasmon, prohexadione-calcium, benzylaminopurine, forchlorfenuron, maleic hydrazide, mepiquat chloride, mefluidide and calcium peroxide.

The paddy seed treatment agent of the present invention may further contain herbicidal injury-reducing agent. Examples of such the herbicidal injury-reducing agent include isoxadifen, isoxadifen-ethyl, oxabetrinil, cloquintcet-mexyl, cyometrinil, dichlormid, dicyclonone, cyprosulfamide, 1,8-Naphthalic Anhydride, fenchlorazole-ethyl, fenclorim, furilazole, fluxofenim, flurazole, benoxacor, mefenpyr, mefenpyr-ethyl, mefenpyr-diethyl, lower alkyl substituted benzoate, PPG-1292 (2,2-dichloro-N-(1,3-dioxane-2-ylmethyl)-N-(2-propenyl) acetamide), MG-191 (2-dichloromethyl-2-methyl-1,3-dioxane), R-29148 (3-dichloroacetyl-2,2,5-trimethyl-1,3-oxazolidine), AD-67 (4-dichloroacetyl-1-oxa-4-azaspiro[4.5] decane), MON4660 (Code No.), N-(2-methoxybenzoyl)-4-[(methylaminocarbonyl)amino] benzenesulfonamide (IUPAC Name, CAS No. 129531-12-0), DKA-24 (N1, N2-diallyl-N2-dichloroacetylglycinamide) and TI-35 (Code No.).

The contents of the coating agent, pesticidal active component, and herbicidal injury-reducing agent may be selected as appropriate depending on the types of the herbicidal active component and the coating agent, and the formulation used.

The paddy seed treatment agent of the present invention may be used for paddy seeds by a seed treatment technique known in the art, for example, the seed dressing method, seed coating method, seed dusting method, seed soaking method, or seed pelleting method. The "dressing method" is a method in which a powder or a wettable powder is sprinkled on seeds. This method is basically a treatment method in which seeds and a powder are placed in a container, and the mixture is stirred to attach the powder to the surface of the seeds. In the dressing method, a liquid agent or a slurry may be used instead of the powder.

The paddy seed treatment agent of the present invention may be used for paddy seeds in a sowable state, or may be used for germinated paddy seeds.

As the paddy seeds used in the present invention, seeds coated with a material to be used for direct sowing cultivation may also be used. Examples of the coating agent used for the paddy seeds of the present invention include iron powders, calcium peroxide, and molybdenum compounds. The coating agent is preferably an iron powder.

The paddy rice herein may be an arbitrary variety of paddy rice. The paddy rice is preferably a variety which is insensitive to the herbicidal active component in the present invention. In the present invention, "insensitive" means that herbicide injury does not occur by treatment with an agent in normal transplantation cultivation in a flooded state. Examples of such a variety of paddy rice include Koshihikari, Hinohikari, Hitomebore, Akitakomachi, Kinuhikari, Nanatsuboshi, Haenuki, Kirara 397, Masshigura, Tsugaru Roman, and Nihonbare.

The compound as the herbicidal active component of the paddy seed treatment agent to be used in the present invention may be used as it is for the treatment of paddy seeds, or a mixture obtained by mixing the compound as the herbicidal active component with a coating agent may be used for the treatment of paddy seeds. If necessary, the paddy seed treatment agent may be mixed with a carrier and another auxiliary agent, and used after formulation into a preparation normally used as a seed treatment agent, for example, a solid preparation such as a powder, wettable powder, or wettable granule; or a liquid preparation such as a solution, emulsion, flowable formulation, or emulsion formulation. The "carrier and another auxiliary agent" herein collectively means synthetic or natural, inorganic or organic substances added to paddy seed treatment agents for aiding delivery of herbicidal active compounds to weeds by controlling their elution, or for simplifying their storage, transportation, or handling.

In the method for treating paddy seeds of the present invention, the paddy seeds are treated with the paddy seed treatment agent of the present invention. The mode of the treatment method is as described above and below.

Treatment of paddy seeds with the paddy seed treatment agent of the present invention may be carried out by using the agent in an amount in which the amount of fenquinotrione or a salt thereof as the herbicidal active component is preferably 0.01 g to 3000 g, more preferably 0.1 g to 1000 g, still more preferably 1 g to 300 g per 1 kg of the seeds. In cases where the paddy seed treatment agent contains an acetolactate synthase-inhibiting herbicidal active compound or a salt thereof, the amount of the acetolactate synthase-inhibiting herbicidal active compound or a salt thereof may be appropriately controlled within the range of preferably 0.01 g to 3000 g, more preferably 0.1 g to 1000 g, still more preferably 1 g to 300 g per 1 kg of the seeds.

In cases where the paddy seeds are coated with the one or more coating agents selected from the group consisting of iron powders, calcium peroxide, and molybdenum compounds described above, coating treatment with the coating agent(s) may be carried out after the treatment of the paddy seeds with the paddy seed treatment agent of the present invention; coating treatment with the coating agent(s) may be carried out before the treatment of the paddy seeds with the paddy seed treatment agent of the present invention; or coating treatment may be carried out using the paddy seed treatment agent of the present invention and the coating agent simultaneously. Thus, the order of treatment is arbitrary. In cases where the simultaneous treatment is carried out, the paddy seed treatment agent and the coating agent may be mixed together, and the resulting mixture may be used for coating treatment of the paddy seeds.

In the present invention, the treatment of paddy seeds with the paddy seed treatment agent needs to be carried out before sowing of the paddy seeds. In terms of its timing, the treatment may be carried out immediately before sowing, or the treatment may be carried out earlier than this, and the treated paddy seeds may be stores until sowing.

The paddy seeds of the present invention are those treated with the paddy seed treatment agent of the present invention. The modes of the paddy seeds and the treatment with the paddy seed treatment agent are as described above and below.

In the method for controlling paddy field weeds of the present invention, the paddy seeds of the present invention are sown and cultivated. The modes of the paddy seeds and the treatment with the paddy seed treatment agent are as described above and below. In the method for controlling paddy field weeds of the present invention, the operation of spraying a herbicide on the paddy field can be omitted, while various weeds that cause problems in the paddy field can be sufficiently controlled, and the risk of herbicide injury to paddy rice can be reduced, so that the labor of paddy cultivation can be largely reduced.

In cases where paddy seeds treated with the paddy seed treatment agent of the present invention are used by direct sowing cultivation, they may be sown on the surface of a paddy field in a flooded state, or may be sown on the surface of a paddy field in a drained state, and the paddy field may be flooded thereafter. Examples of the flooded direct sowing cultivation method include mechanical-type or compressed-air-blowing-type row sowing methods, spraying methods using a knapsack power sprayer or a radio-controlled helicopter, and hill sowing methods using a shooting hill-seeder combined with a paddy harrow. Alternatively, after cultivating the soil in a flooded state, the water may be once drained, and flooding may be carried out after the seedlings have grown to some extent. From the viewpoint of suppressing herbicide injury to the paddy seeds according to the present invention by treatment with the paddy seed treatment agent, and securing the herbicidal effect, it is preferred to flood the field for seven days after the sowing, and to keep the field drained until budding of the rice thereafter.

The paddy seed treatment agent, the method for treating a paddy seed(s), the paddy seed, and the method for controlling paddy field weeds, of the present invention are applicable to paddy cultivation, and they can achieve saving of the labor of spraying a herbicide, control of serious weeds, and reduction of the risk of herbicide injury to paddy rice. Thus, these are excellent inventions.

EXAMPLES

The present invention is described below concretely by way of Preparation Example of paddy seeds treated with the paddy seed treatment agent to be used in the present invention, and Test Example on weed control. However, the present invention is not limited to these.

Preparation Example: Treatment of Iron-coated Paddy Seeds with Paddy Seed Treatment Agent Treatment of dried paddy seeds was carried out at a coating ratio of 0.5 (seeds:iron powder=1:0.5). More specifically, paddy seeds, an iron powder, and calcined gypsum were mixed and stirred together while spraying water thereon, using a coating machine according to a conventional method, to coat the seeds with the iron powder and the calcined gypsum. The outer layer of the coated seeds was further similarly coated with finishing calcined gypsum mixed with each of the paddy seed treatment agents containing the herbicidal active components shown in Tables 2 to 6. The amounts of the materials used are shown in Table 1.

TABLE 1

| Amount of Each Material per 1 kg of Dried Seeds | |
|---|---|
| Dry unhulled rice | 1 kg |
| Iron powder | 0.5 kg |
| Mixing calcined gypsum | 0.05 kg |
| Finishing calcined gypsum | 0.05 kg |

Test Example 1

In a 200-cm² plastic pot, paddy field soil was placed, and tillage was carried out, followed by sowing seeds of *Echinochloa oryzicola* and *Scirpus juncoides* on the soil surface. Then, tubers of *Eleocharis kuroguwai* in the germination state were buried in such a manner that tips of the sprouts in tubers are exposed to the outside of the soil surface. Four paddy seeds treated with each paddy seed treatment agent obtained in Preparation Example were sown, and water was gently introduced to allow flooding to a depth of 4 cm. On Day 7 after the sowing, the water was removed by suction. When the rice seedlings have grown to the one-leaf stage, flooding was allowed again to a depth of 4 cm. On Day 15 after the sowing, the germination rate of the paddy seeds and the growth-inhibitory effect on the weeds were judged. The results are shown in Table 2 to Table 5. The germination rate of the paddy seeds is expressed as %, and the growth-inhibitory effect on the weeds is expressed as a value of 0 to 100 representing the degree of inhibition, wherein 0 represents no inhibition, and 100 represents complete death.

TABLE 2

| | Effective component of paddy seed treatment agent | Amount of agent per 1 kg of paddy seeds (a.i. g) | Germination rate of paddy rice (%) | Growth-inhibitory rate for *Scirpus juncoides* |
|---|---|---|---|---|
| Example 1 | Fenquinotrione | 7.5 | 100 | 90 |
| Comparative Example 1 | Tefuryltrione | 7.5 | 50 | 80 |
| Comparative Example 2 | Benzobicyclon | 5.0 | 50 | 85 |
| Comparative Example 3 | None (Iron coating alone) | 0 | 100 | 0 |

TABLE 3

| | Effective component of paddy seed treatment agent | Amount of agent per 1 kg of paddy seeds (a.i. g) | Germination rate of paddy rice (%) | Growth-inhibitory rate for *Echinochloa oryzicola* | Growth-inhibitory rate for *Scirpus juncoides* |
|---|---|---|---|---|---|
| Example 2 | Fenquinotrione<br>Pyrimisulfan | 7.5<br>1.25 | 100 | 95 | 100 |
| Comparative Example 4 | Tefuryltrione<br>Pyrimisulfan | 7.5<br>1.25 | 50 | 75 | 90 |
| Comparative Example 5 | Benzobicyclon<br>Pyrimisulfan | 5.0<br>1.25 | 75 | 90 | 95 |
| Comparative Example 6 | None (Iron coating alone) | 0 | 100 | 0 | 0 |

TABLE 4

| | Effective component of paddy seed treatment agent | Amount of agent per 1 kg of paddy seeds (a.i. g) | Germination rate of paddy rice (%) | Growth-inhibitory rate for *Echinochloa oryzicola* | Growth-inhibitory rate for *Scirpus juncoides* |
|---|---|---|---|---|---|
| Example 3 | Fenquinotrione<br>Pyriminobac-methyl<br>Bensulfuron-methyl | 7.5<br>1.5<br>1.25 | 100 | 100 | 100 |
| Comparative Example 7 | Tefuryltrione<br>Pyriminobac-methyl<br>Bensulfuron-methyl | 7.5<br>1.5<br>1.25 | 75 | 100 | 90 |
| Comparative Example 8 | Benzobicyclon<br>Pyriminobac-methyl<br>Bensulfuron-methyl | 5.0<br>1.5<br>1.25 | 75 | 100 | 90 |
| Comparative Example 9 | None (Iron coating alone) | 0 | 100 | 0 | 0 |

TABLE 5

| | Effective component of paddy seed treatment agent | Amount of agent per 1 kg of paddy seeds (a.i. g) | Germination rate of paddy rice (%) | Growth-inhibitory rate for *Echinochloa oryzicola* | Growth-inhibitory rate for *Eleocharis kuroguwai* |
|---|---|---|---|---|---|
| Example 4 | Fenquinotrione<br>Pyriminobac-methyl<br>Pyrimisulfan | 7.5<br>1.5<br>1.25 | 100 | 100 | 90 |
| Comparative Example 10 | Tefuryltrione<br>Pyriminobac-methyl<br>Pyrimisulfan | 7.5<br>1.5<br>1.25 | 50 | 100 | 70 |

TABLE 5-continued

| | Effective component of paddy seed treatment agent | Amount of agent per 1 kg of paddy seeds (a.i. g) | Germination rate of paddy rice (%) | Growth-inhibitory rate for Echinochloa oryzicola | Growth-inhibitory rate for Eleocharis kuroguwai |
|---|---|---|---|---|---|
| Comparative Example 11 | Benzobicyclon Pyriminobac-methyl Pyrimisulfan | 5.0 1.5 1.25 | 75 | 100 | 70 |
| Comparative Example 12 | None (Iron coating alone) | 0 | 100 | 0 | 0 |

Test Example 2

In a 200-cm$^2$ plastic pot, paddy field soil was placed, and tillage was carried out, followed by sowing seeds of *Scirpus juncoides* on the soil surface. Then, the seeds were covered with 0.5-cm thick soil. Subsequently, flooding was allowed to a depth of 4 cm, followed by sowing seeds of *Monochoria vaginalis* on the soil surface. When the *Monochoria vaginalis* reached the five-leaf stage, three paddy seeds treated with each paddy seed treatment agent obtained in Preparation Example were sown. On Day 22 after the sowing of paddy seeds, the germination rate of the paddy seeds and the growth-inhibitory effect on the weeds were judged. Since *Lindernia* species were spontaneously grown in the test field soil, the growth-inhibitory effect on the *Lindernia* species were also judged. The results are shown in Table 6. The germination rate of the paddy seeds is expressed as %, and the growth-inhibitory effect on the weeds is expressed as a value of 0 to 100 representing the degree of inhibition, wherein 0 represents no inhibition, and 100 represents complete death.

TABLE 6

| | Effective component of paddy seed treatment agent | Amount of agent per 1 kg of paddy seeds (a.i. g) | Germination rate of paddy rice (%) | Growth-inhibitory rate | | |
|---|---|---|---|---|---|---|
| | | | | *Scirpus juncoides* | *Monochoria vaginalis* | *Lindernia species* |
| Example 5 | Fenquinotrione | 7.5 | 100 | 98 | 95 | 95 |
| Comparative Example 13 | Pyrazolate | 75 | 100 | 70 | 67 | 53 |
| Comparative Example 14 | None (Iron coating alone) | 0 | 100 | 0 | 0 | 0 |

The invention claimed is:

1. A method for treating a paddy seed(s), said method comprising coating a paddy seed(s) prior planting with a paddy seed treatment agent comprising fenquinotrione or a salt thereof as a herbicidal active component.

2. The method for treating a paddy seed(s) according to claim 1, wherein said paddy seed treatment agent further comprises an acetolactate synthase-inhibiting herbicidal active compound or a salt thereof as a herbicidal active component.

3. The method for treating a paddy seed(s) according to claim 1, wherein said paddy seed(s) is/are coated with said paddy seed treatment agent in an amount in which the amount of said fenquinotrione or a salt thereof is within the range of 0.01 g to 3000 g per 1 kg of said paddy seed(s).

4. The method for treating a paddy seed(s) according to claim 2, wherein said paddy seed(s) is/are coated with said paddy seed treatment agent in an amount in which the amount of said acetolactate synthase-inhibiting herbicidal active compound or a salt thereof is within the range of 0.01 g to 3000 g per 1 kg of said paddy seed(s).

5. The method for treating a paddy seed(s) according to claim 1, wherein, after said coating of said paddy seed(s) with said paddy seed treatment agent, coating treatment with one or more coating agents selected from the group consisting of iron powders, calcium peroxide, and molybdenum compounds is carried out.

6. The method for treating a paddy seed(s) according to claim 1, wherein, before said coating of said paddy seed(s) with said paddy seed treatment agent, coating treatment with one or more coating agents selected from the group consisting of iron powders, calcium peroxide, and molybdenum compounds is carried out.

7. The method for treating a paddy seed(s) according to claim 1, wherein said paddy seed treatment agent is mixed with one or more coating agents selected from the group consisting of iron powders, calcium peroxide, and molybdenum compounds, and said paddy seed(s) is/are subjected to coating treatment with the resulting mixture.

8. A paddy seed(s) coated with a paddy seed treatment agent comprising fenquinotrione or a salt thereof as a herbicidal active component.

9. A method for controlling paddy field weeds, said method comprising sowing and cultivating the paddy seed(s) according to claim 8.

10. The method for treating a paddy seed(s) of claim 2, wherein said acetolactate synthase-inhibiting herbicidal active compound is one or more compounds selected from the group consisting of sulfonyl urea compounds, imidazolinone compounds, triazolopyrimidine compounds, pyrimidinyl carboxy compounds, and sulfonylaminocarbonyltriazolinone compounds.

11. The method for treating a paddy seed(s) of claim 10, wherein said pyrimidinyl carboxy compound is pyrimisulfan.

* * * * *